United States Patent [19]

Küpper et al.

[11] Patent Number: 5,091,594
[45] Date of Patent: Feb. 25, 1992

[54] PROCESS FOR THE PRODUCTION OF 2,6-DI-TERT-BUTYLPHENOL

[75] Inventors: Friedrich-Wilhelm Küpper; Wolfgang H. E. Müller; Alfred Oberholz, all of Marl, Fed. Rep. of Germany

[73] Assignee: Huels Aktiengesellschaft, Marl, Fed. Rep. of Germany

[21] Appl. No.: 625,400

[22] Filed: Dec. 11, 1990

[30] Foreign Application Priority Data

Dec. 15, 1989 [DE] Fed. Rep. of Germany ....... 3941472

[51] Int. Cl.$^5$ ....................... C07C 37/11; C07C 37/14
[52] U.S. Cl. .................... 568/789; 568/784; 568/785; 568/794
[58] Field of Search ............... 568/789, 784, 790, 798, 568/780, 785, 794

[56] References Cited

U.S. PATENT DOCUMENTS

| | | | |
|---|---|---|---|
| 3,355,504 | 11/1967 | Coffield et al. | 568/789 |
| 4,631,349 | 12/1986 | Goins et al. | 568/789 |
| 4,870,215 | 9/1989 | Wilker et al. | 568/789 |

FOREIGN PATENT DOCUMENTS

| | | | |
|---|---|---|---|
| 1809555 | 10/1969 | Fed. Rep. of Germany | 568/789 |
| 3188635 | 8/1989 | Japan | 568/789 |

Primary Examiner—Werren B. Lone
Attorney, Agent, or Firm—Millen, White & Zelano

[57] ABSTRACT

For producing 2,6-di-tert-butylphenol and products therefrom, utilizing small quantities of aluminum tris-(2-tert-butylphenolate as a catalyst by reaction of 2-tert-butylphenol with isobutene in the liquid phase, the reaction is performed in the presence of diluents such as liquid saturated aliphatic or cycloaliphatic hydrocarbons, $C_5$–$C_{16}$ alkenes of formula $R_1$—CH=$CH_2$ or $R_2$—CH=CH—$R_3$, $C_5$ to $C_{12}$ cycloalkenes, which contain no branching on the C=C-bond, excess isobutene or mixtures thereof, at temperatures of 0° C. to 80° C., pressures of 0.1 to 11 bars and catalyst amounts of 0.005 to 5 mol %, based on 2-tert-butylphenol. High conversions are obtained with few undesirable trialkylated products.

19 Claims, No Drawings

PROCESS FOR THE PRODUCTION OF 2,6-DI-TERT-BUTYLPHENOL

BACKGROUND OF THE INVENTION

The invention relates to an improved process for the production of 2,6-di-tert-butylphenol with increased selectivity at low pressure and low temperatures by the reaction of 2-tert-butylphenol with isobutene under catalysis with aluminum tris-(2-tert-butylphenolate) in the presence of (1) saturated aliphatic and/or cycloaliphatic hydrocarbons and/or (2) excess liquid or dissolved isobutene and/or (3) $C_5$ to $C_{12}$ cycloalkenes, which contain no branchings in the C=C bond, and/or (4) alkenes of formula $R_1$—CH=$CH_2$ (1-alkenes) or $R_2$—CH=CH—$R_3$ with 5 to 16 C atoms.

It is known that 2,6-di-tert-butylphenol can be obtained by the addition of isobutene to phenol or to 2-tert-butylphenol in the presence of aluminum phenolates (cf. Ullmann, "Enzyklopaedie der Technischen Chemie [Encyclopedia of Industrial Chemistry]," Volume 18 (1979), page 205 ff.). The alkylation of phenol or 2-tert-butylphenol is usually performed in the presence of aluminum phenolate at 100° C. and above, typically at 110° C. to 120° C., under pressure, which can be up to 25 bars. The catalyst is obtained by dissolving 1 to 3% by weight of aluminum in the phenol to be alkylated [cf. US-PS 2 831 898, DE-PSS 944 014, 1 044 825; J. Org. Chem. 22 (1957) 642; Ang. Chem. 69 (1957) 699]. It can also be produced by the reaction of aluminum alcoholates or of triethyl aluminum with phenol, as well as by other methods. The 2-tert-butylphenol or 2,6-di-tert-butylphenol obtained is a function of the ratio of the respective phenol used to the isobutene. Both 2,4-di-tert-butylphenol and 2,4,6-tri-tert-butylphenol occur as by-products. The use of excess isobutene results in high yields of the trisubstituted phenol [cf. Ullmann, "Enzyklopaedie der Technischen Chemie," Volume 18 (1979), p. 200; Kirk-Othmer, "Encyclopedia of Chemical Technology," Vol. 2 (1978), p. 85)]. In addition, with increasing reaction time, there is an increase in the portion of compounds containing a para-position tert-butyl substituent (2,4-di-tert-butylphenol, 2,4,6-tri-tert-butylphenol). Therefore, the reaction is interrupted at an optimal moment for the production of 2,6-di-tert-butylphenol. At the end of the alkylation, the aluminum phenolate catalyst is deactivated, at the latest, before the separation of the reaction products by distillation to avoid dealkylation of the products. In general, this deactivation takes place by hydrolysis with water, acid or diluted lye, but even traces of acids have to be removed or neutralized again before the distillation. This requires (cf. Ullmann, p. 202) a careful washing of the alkylate with lye and water, and waste water results, which (after separating of the aqueous phase) has to be subsequently treated, to avoid polluting the environment. The rectification of the organic phase obtained according to this production process yields, for example, with the use of 2 mol of isobutene per mole of phenol, about 75% of theory of 2,6-di-tert-butylphenol and about 10% of theory of 2-tert-butylphenol. The distillation residue consists primarily of 2,4,6-tri-tert-butylphenol. Alternatively, if only 1 mol of isobutene per mole of phenol is used, then in addition to unreacted phenol and some 2,6-di-tert-butylphenol, 2-tert-butylphenol is isolated as the main product, which is obtained in about a 70% yield in relation to the reacted phenol.

If the catalyst is produced from aluminum organic compounds, preferably trialkyl aluminum, and 2-tert-butylphenol instead of the phenol, the addition of isobutene to 2-tert-butylphenol is successful even at temperatures below 100° C. (cf. U.S. Pat. No. 3,355,504). Despite the lower reaction temperatures, the alkylation quickly produces the desired 2,6-di-tert-butylphenol, and with the use of comparable catalyst amounts (about 1-3 mol % in relation to the 2-tert-butylphenol used), this compound yields smaller portions of undesirable admixtures (such as 2,4-di-tert-butylphenol or above all, 2,4,6-tri-tert-butylphenol). Also, this special catalyst system must be deactivated before the beginning of the working up so as to avoid the dealkylation and realkylation during the separation of the reaction products by distillation.

Independent of the type of aluminum containing catalyst used, obtaining 2,6-di-tert-butylphenol by alkylation of phenol or 2-tert-butylphenol is always performed without using solvents according to the process of the prior art [cf. Ullmann, "Enzyklopaedie der Technischen Chemie," Volume 18 (1979), p. 202]. In this way, the isobutene is added so quickly as to allow the removal of heat from the reactor. This is necessary since the exact adherence to a narrow temperature range is a prerequisite for the production of 2,6-di-tert-butylphenol with the indicated yields (of about 75% of theory) in using the aluminum tris(phenolate) catalyst (cf. Ullmann, pp. 205/206). Obviously, this is mainly used. On the other hand, in the case of the alkylation of 2-tert-butylphenol in the presence of the aluminum tris-(2-tert-butylphenolate) catalyst, a considerable temperature increase is observed within a few minutes after the addition of isobutene [cf. U.S. Pat. No. 3,355,504, examples 2 and 3], which makes the production of 2,6-di-tert-butylphenol at a constant, low reaction temperature difficult and may make it impossible on a larger scale.

Disadvantages in the older processes of the prior art are in their need for relatively large amounts of the only moderately active aluminum tris-(phenolate) catalyst, which just as the aluminum tris-(2-tert-butylphenolate) catalyst, must be deactivated before the separation of the reaction products by distillation. The removal of the resulting waste water containing aluminum compounds and (alkyl-)phenols is absolutely necessary for reasons of environmental protection, but not without problems. This is indicated by the number of patent applications which deal with the deactivation of catalysts as well as with quite costly solutions to the disposal of waste water or with the reduction of the resulting amount (cf., e.g., U.S. Pat. No. 3,200,157, DE-PS 1 809 555, DE-OS 2 039 062, U.S. Pat. No. 3,939,215, DE-PS 2 602 149, BE-PS 842 691, U.S. Pat. No. 3,652,685, U.S. Pat. No. 3,970,708). The problems connected with the removal of waste water thus far could not be solved by heterogenization of known catalysts (cf. EP 206 085), since the catalytically effective aluminum phenolate catalysts are discharged with the reaction products to a significant extent.

Another drawback of the processes of the prior art consists in the formation of a high portion of undesirable di- and above all tri-alkylated products when using the aluminum tris-(phenolate) catalyst for the addition of isobutene to phenol. The separation and purification by distillation of the desired 2,6-di-tert-butylphenol are thus made considerably more difficult, and a significant portion of material used cannot easily be converted into usable products. The process of U.S. Pat. No. 3,355,504 makes it possible to considerably reduce the portion of 2,4,6-tri-tert-butylphenol and to produce 2,6-di-tert-butylphenol with yields of about 93% of theory. However, also in this process, the removal of the reaction heat and the adherence to a specified temperature in using the catalyst amounts indicated in examples 2 and 3, is similarly difficult as in the conventional process. In this process—as already mentioned—the isobutene feed optionally has to be matched to the heat removal to keep the reaction temperature in the required range, and finally, after an optimal 2,6-di-tert-butylphenol portion is reached, must be quickly and completely interrupted to prevent the formation of considerable portions of the undesirable 2,4,6-tri-tert-butylphenol. The production of 2,4,6-tri-tert-butylphenol influences the economic efficiency of the usual processes greatly so that its recycling into the alkylation process was recommended despite a considerable degree of technical complexity and only a modest increase of the 2,6-di-tert-butylphenol yields. (cf. U.S. Pat. No. 4,560,809). The process performed at about 100° C., moreover, requires (1) technical devices for heating the reactor when the catalyst is formed (from aluminum) and at the beginning of the alkylation and (2) efficient cooling devices for temperature control during the reaction.

SUMMARY OF THE INVENTION

Since the known processes of the prior art exhibit the described drawbacks, an object of the invention is to develop an improved nonpolluting process for the production of 2,6-di-tert-butylphenol with increased yields at low catalyst consumption as well as a reduced portion of 2,4,6-tri-tert-butylphenol and 2,4-di-tert-butylphenol in the reaction product.

It is possible to achieve this object in a manner requiring low technical expense, by producing the 2,6-di-tert-butylphenol from the addition of isobutene to 2-tert-butylphenol under catalysis with aluminum tris-(2-tert-butylphenolate) in the presence of (1) saturated aliphatic and/or cycloaliphatic hydrocarbons and/or (2) $C_5$ to $C_{12}$ cycloalkenes, which contain no branchings on the C=C bond, and/or (3) alkenes of the formula $R_1$—CH=$CH_2$ (1-alkenes) or $R_2$—CH=CH—$R_3$ with 5 to 16 C atoms and/or of (4) excess liquid or dissolved isobutene at temperatures as low as possible using amounts of catalyst as small as possible.

It is another object of the invention to provide a process for the production of 2,6-di-tert-butylphenol by the reaction of 2-tert-butylphenol with isobutene in the liquid phase at temperatures in the range of 0° to 80° C. and pressure of from 0.1 bar to 11 bars in the presence of 0.005 to 5 mole% of aluminum tris-(2-tert-butylphenolate) catalyst, based on 2-tert-butylphenol, characterized in that the reaction is performed in the presence of a diluent which is one or more saturated aliphatic hydrocarbons, one or more saturated cycloaliphatic hydrocarbons, excess liquid or dissolved isobutene, one or more $C_5$ to $C_{16}$ alkenes of formulas $R_1$—CH=$CH_2$ or $R_2$—CH=CH—$R_3$, where $R_1$, $R_2$ and $R_3$ are alkyl, one or more $C_5$ to $C_{12}$ cycloalkenes which contain no branchings in the C=C bond, or mixtures thereof.

This solution is extraordinarily surprising, since only the addition of the known solvents in considerable amounts or even more surprisingly, an excess of liquid or dissolved isobutene under the conditions according to the invention results in the desired improvements with respect to the portion of 2,4-di-tert-butylphenol and above all, of 2,4,6-tri-tert-butylphenol.

In U.S. Pat. No. 3,355,504, the disadvantages of a high content of 2,4,6-tri-tert-butylphenol are specifically pointed out, and the advantages attained in comparison with the prior art (e.g., the process of U.S. Pat. No. 2,831,898) are emphasized. Thus, in U.S. Pat. No. 3,355,504, for example, it is recommended to perform the alkylation of phenol with isobutene in the presence of aluminum tris-(phenolate) above 90° C. at about 7 bars, until the content of 2-tert-butylphenol and 2,6-di-tert-butylphenol heads for a maximum, while, on the other hand, only a small portion of at most 5 to 6 percent of the undesirable 2,4,6-tri-tert-butylphenol has formed. Then, according to U.S. Pat. No. 3,355,504 (cf. column 3, line 10 ff.), the reaction temperature is to be lowered to below 90° C. The reaction is then continued at lower temperature after addition or formation of an aluminum (2-alkylphenolate) catalyst. Thus, first an equivalent stoichiometric amount of reactive "aluminum salt," is added to the unreacted phenol and optionally present (phenol-)ethers, which reacts with the phenol to form aluminum phenolate and with the (phenol-)ethers to form complexes (cf. column 3, line 70 ff. and column 4, line 1 ff.), before an excess of 0.001 to 5.0 mol %, preferably of 0.001 to 1 mol %, reactive "aluminum salt," in relation to the 2-tert-butylphenol present, causes the further catalytic reaction. A greater excess of reactive aluminum compound, i.e. portions of up to 50 mol % and more, is indeed excessive in itself, but according to the data of U.S. Pat. No. 3,355,504 can be added without drawback. The aluminum compounds as such can be added to the reaction mixture directly but also in the form of solutions in inert solvents such as hexane, benzene or toluene. The solvents in this case are used only in small amounts (cf. column 6, line 8 ff.). Isolation of aluminum tris-(2-tert-butylphenolate) from hexane-containing 2-tert-butylphenol and washing of the filtered precipitate with n-hexane are described.

According to the preferred two-stage embodiment of U.S. Pat. No. 3,355,504, determination of the time at which the respectively of 2-tert-butylphenol and 2,6-di-tert-butylphenol is reached before lowering the temperature to less than 90° C., preferably less than 60° C., and continuing the reaction following formation of the catalyst containing 2-tert-butylphenolate radicals, is difficult. Quick cooling of the reaction mixture to the required lower temperature and determination of the necessary minimal amounts of reactive "aluminum salt" (aluminum alkyls) to be added are certainly linked with a considerable technical and analytical effort. To assure the continuation of the alkylation, the addition of a considerable excess of aluminum alkyls, in amounts at least near the upper limit of the optimal range (from 0.001 to 1 mol %) is required.

As a consequence, in working up such reaction mixtures, considerable amounts of aluminum-containing catalysts or complexes have to be disposed of without polluting the environment, since in addition to the aluminum tris-phenolate used first at higher than 90° C., the catalyst effective at a lower temperature is also present and the reaction products formed previously from reaction with phenol, (phenol-)ethers and aluminum alkyls. In view of the efforts described in the prior art for necessary catalyst deactivation and removal, the steps in the two-stage process preferred in U.S. Pat. No. 3,355,504 are likely to cause high costs today, which again would at least partially offset the advantage of the reduced 2,4,6-tri-tert-butylphenol portions.

In the one-stage process according to U.S. Pat. No. 3,355,504, the addition of isobutene to 2-tert-butylphenol proceeds quickly in the presence of the catalyst amounts used in examples 2 and 3 and—despite the small amounts of 2-tert-butylphenol used—under rapid evolution of heat. Catalyst formation and alkylation take place in the presence of some toluene. The observed portions of by-products of 2,6-di-tert-butylphenol synthesis, such as, e.g., 2,4,6-tri-tert-butylphenol, were not indicated. No teaching can be gathered either from the description or the examples of the specification whether such a process can be transferred problem-free on a large scale and whether in doing so 2,4,6-tri-tert-butylphenol is formed in only small amounts.

In view of the described drawbacks and the unclear teachings in certain areas of the prior art, as it is represented by U.S. Pat. No. 3,355,504, it was surprising that the difficulties connected with this long known process can be solved by the specific addition of considerable amounts of selected solvents, which are available at a reasonable price in unlimited amounts and are easy to separate or recover after completed reaction, as well as by selection of specific features of the process with respect to the type and the amount of the catalyst to be used and the reaction conditions to be met. Only such a combination of measures and exact adherence to all these conditions lead to success and makes possible the synthesis of 2,6-di-tert-butylphenol with considerably smaller portions of 2,4,6-tri-tert-butylphenol. The presence of the solvents to be used according to the invention, moreover, facilitates the dissipation of the nascent reaction heat and allows for the presence of a considerable excess of isobutene even after a substantial conversion of the 2-tert-butylphenol used. Finally, the removal of the catalyst to be deactivated by hydrolysis or other means causes only a fraction of the problems which are characteristic of the processes of the prior art because of the small amounts used according to the invention.

According to the process of the invention, 2,6,-di-tert-butylphenol can be produced from 2-tert-butylphenol and isobutene with smaller portions of 2,4,6-tri-tert-butylphenol, by a) using aluminum tris-(2-tert-butylphenolate) as a catalyst in amounts of 0.005 to 5 mol %, preferably of 0.05 to 0.8 mol % and especially preferably of 0.1-0.5 mol %, in relation to the 2-tert-butylphenol used, b) adding isobutene at temperatures of 0° C. to 80° C., preferably of 5° to 50° C. and most preferably 10° C. to 20° C. as well as at pressures 0.1 to 11 bars, preferably 0.2 to 6.0 bars and most preferably 0.5 to 2.5 bars, c) performing the reaction in the liquid phase in the presence of (1) saturated aliphatic and/or cycloaliphatic hydrocarbons, which preferably contain 5 to 10 carbon atoms, and/or (2) excess liquid or dissolved isobutene and/or (3) $C_5$ to $C_{16}$ alkenes of formula $R_1—CH=CH_2$ or $R_2—CH=CH—R_3$ where $R_1$, $R_2$ and $R_3$ are alkyl, and/or, (4) $C_5-C_{12}$ cycloalkenes which contain no branchings in the C=C bond and the saturated alkanes or cycloalkanes are preferably used similar to isobutene, and d) adding said liquid or dissolved diluents under reaction conditions in amounts of i) 20 to 1,000 parts by weight, preferably of 40 to 500 parts by weight and especially preferably of 60 ,to 200 parts by weight in relation to 100 parts by weight of 2-tert-butylphenol and isobutene in a molar excess of 0 2 to 10 mol, preferably 1 to 5 mol, especially preferably of 1.1 to 2.5 mol, in relation to 1 mol of 2-tert-butylphenol, or ii) in the case of isobutene, the latter should be present in a molar excess of 2 to 10 mol, preferably of 2.2 to 5 mol, per mol of 2-tert-butylphenol. It is recommended to keep the catalyst amount small even with the addition of considerable amounts of diluents.

Especially preferred as diluents are saturated aliphatic or cycloaliphatic hydrocarbons such as, e.g., hexane, cyclohexane, ethylcyclohexane, isopropylcyclohexane (hydrocumol) or Decalin. With the use of alkenes and cycloalkenes, such as, e.g., cyclohexene, cis-cyclooctene, or octene-1, small portions of higher-boiling phenolic by-products can result, whose separation by distillation from the desired 2,6-di-tert-butylphenol (with a suitable selection of the C number of these alkenes and cycloalkenes) is simpler than that of the 2,4,6-tri-tert-butylphenol, whose portion is reduced significantly.

The 2-tert-butylphenol and the diluents must be free of water and catalyst poisons.

By the term aluminum tris-(2-tert-butylphenolate) are also meant catalysts, in which one of the 2-tert-butylphenolate radicals can be replaced by other groups—as stated in U.S. Pat. No. 3,355,504.

The 2,6-di-tert-butylphenol that can be produced in better yields with greater selectivity and in higher purity according to the process of the invention is a sought after compound from which valuable secondary products, above all in the field of phenolic antioxidants, can be obtained.

The process according to the invention is explained in more detail by the following examples.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius and unless otherwise indicated, all parts and percentages are by weight.

The entire disclosures of all applications, patents and publications, cited above and below, and of corresponding application Federal Republic of Germany P 39 41 472.8-44, filed Dec. 15, 1989, are hereby incorporated by reference.

EXAMPLES

Alkylations of 2-tert-butylphenol (abbr. 2-TBP) with isobutene were performed in a stirring autoclave at the highest possible stirring rpm (less than or equal to 1400 rpm). Cooling or temperature control of the reactor took place with a high-performance thermostat. A thermocouple attached inside the reactor allowed the recording of the reaction temperature. Changes in the reactor level were followed by a suitable measuring device. Samples for gas chromatographic analyses were gathered by a port on the reactor. The catalyst contained in the samples was deactivated by adding some drops of water before the portions of the various components of the reaction mixtures were determined by gas chromatography. Optionally present admixtures of solvents were not taken into consideration in the evaluation of the analyses, i.e. the data contained in the following tables on the various examples describe the composition (in % by weight) of "solvent-free" reaction mixtures. In this connection, the following abbreviations were always used:

2-TBP = 2-tert-butylphenol
2,4-DTBP = 2,4-di-tert-butylphenol
2,6-DTBP = 2,6-di-tert-butylphenol
2,4,6-TTBP = 2,4,6-tri-tert-butylphenol.

The indicated values of the selectivity (abbr. S) of the formation of 2,6-di-tert-butylphenol are related to the reacted 2-tert-butylphenol. In all alkylations indicated in the examples, 250 g (1.66 mol) each of 2-tert-butylphenol was introduced in the dry stirring autoclave, optionally the indicated amounts of the various solvents were added, and then the desired portions of the catalyst were formed by adding -triethyl aluminum, dissolved in (cyclo)aliphatic hydrocarbons, after the reaction mixture and reactor had been previously freed of air (or oxygen residues) by flushing with inert gas. After removal of the released ethane, the reactor was closed and its content temperature controlled. At the desired reaction temperature, the isobutene was then added by vigorous thorough mixing in the planned amounts. The alkylations performed isothermally were generally completed as soon as high portions of the 2,6-di-tert-butylphenol were reached or no further significant decrease of the 2-tert-butylphenol content could be observed.

Because the catalyst system is used in only small amounts and it is sensitive toward specific admixtures, comparisons are advisable only within a series of tests, in which the same batches of educt, solvent and aluminum triethyl were used.

For reasons of clarity, the excess of isobutene used is always indicated in the tables, i.e. the difference between added total amount of isobutene and the amount of isobutene (1.66 mol) necessary in the complete conversion of the 2-tert-butyl-phenol amount used to 2,6-DTBP. In most tests according to the process of the invention, the operation was performed with larger isobutene excess than in the comparison tests according to the prior art. The pressures indicated in bars are the total pressures (absolute pressures) set in the system.

EXAMPLES 1 TO 8

These examples do not illustrate the present invention. In the way described previously, 250 g (1.66 mol) of 2-tert-butylphenol was reacted at 1.5 bars with a limited excess of isobutene in the presence of different amounts of aluminum tris-(2-tert-butylphenolate) at 10° C. or 30° C. Table 1 contains the portions of alkylphenols in the reaction mixtures observed after various reaction times.

In all cases, a high portion of 2,4,6-tri-tert-butylphenol is observed as soon as the 2-tert-butylphenol used is largely consumed and converted in different degree to 2,6-di-tert-butylphenol (cf., e.g., example 5 with example 9, example 6 with example 10, example 8 with example 12, etc.).

EXAMPLES 9 TO 12 (cf. TABLE I)

In the procedure applied in examples 1 to 8, 2-tert-butylphenol was alkylated at 10° C. or 30° C. in the presence of small catalyst amounts at a pressure of 2.5 to 2.8 bars with a marked excess of isobutene. As a result, the portion of the undesirable 2,4,6-tri-tert-butylphenol in comparison with the prior art was kept at a lower level even where high conversion of 2-tert-butylphenol was obtained.

EXAMPLES 13 TO 30 (cf. TABLE II)

According to the previously described procedure, 250 g (1.66 mol) of 2-tert-butylphenol was alkylated in the presence of the indicated small amounts of aluminum tris-(2-tert-butylphenolate) at 10° C. or 30° C. with an excess of isobutene at a pressure of 1.5 to 2.8 bars. In this case, different amounts of different solvents were added.

It is recognized that in the absence of (cyclo)aliphatic solvents to be added according to the invention, higher portions of 2,4,6-tri-tert-butylphenol (and correspondingly lower selectivities during the formation of 2,6-di-tert-butylphenol) are observed under comparable reaction conditions. With toluene (as a representative of aromatic solvents), a significant lowering of the content of 2,4,6-tri-tert-butylphenol could not be attained.

EXAMPLES 31 TO 59 (cf. TABLES III AND IV)

In the procedure applied in examples 1 to 30, 250 g (1.66 mol) of 2-tert-butylphenol was alkylated in the presence of 1.9 to 8.5 mmol of aluminum tris-(2-tert-butylphenolate) with an excess of isobutene at 1.4 to 1.5 bars. The results show that by using increasing amounts of solvents according to the invention, improved selectivities in the formation of 2,6-di-tert-butylphenol can be achieved and that under such conditions, even with a high excess of isobutene, even after considerably lengthened reaction times, only a small increase of the portion of 2,4,6-tri-tert-butylphenol can be observed.

In the same way, the reduction of the amount of catalyst or of the reaction temperature has advantageous effects in the presence of the solvents to be used according to the invention. Comparable improvements cannot be achieved with toluene or m-xylene under identical reaction conditions but with the solvents ethylcyclohexane, isopropylcyclohexane or Dekalin, whose use according to the process of the invention should also be advantageous.

EXAMPLES 60 to 63 (cf. TABLE V)

In the procedure applied in examples 1 to 59, 250 g (1.66 mol) of 2-tert-butylphenol was reacted with an excess of isobutene at a pressure of 1.5 bars and a reaction temperature of 10° C. in the presence of 5.7 mmol of aluminum tris-(2-tert-butylphenolate). In the presence of 200 ml each of various olefins to be added according to the invention, the portion of the undesirable 2,4,6-tri-tert-butylphenol was able to be markedly reduced, without formation of a comparable portion of undesirable admixtures, difficult to separate by distillation. These results were obtained where even the reaction time was lengthened considerably over the other wise usual period or the period necessary to achieve a high conversion of 2-tert-butylphenol.

TABLE I

Production of 2,6-di-tert-butylphenol from 2-tert-butylphenol

| Example No. | Catalyst Amount (mmol) | Excess of isobutene (mol) | Pressure (bar) | Reaction temp. (°C.) | Reaction time (hours) | 2-TBP | 2,6-DTBP | 2,4-DTBP | 2,4,6-TTBP• | Selectivity S |
|---|---|---|---|---|---|---|---|---|---|---|
| 1* | 45 | 1.5 | 1.4 | 10–30 | 0.7 | 3.7 | 89.0 | 0.3 | 6.3 | 94.4 |
| 2* | 22.5 | 1.6 | 1.5 | 10 | 0.7 | 9.4 | 85.8 | 0.3 | 4.0 | 96.1 |
|  | 22.5 | 1.6 | 1.5 | 10 | 1.0 | 1.4 | 93.3 | 0.1 | 4.7 | 96.1 |
| 3* | 11.3 | 1.6 | 1.5 | 10 | 0.7 | 24.1 | 71.6 | 0.7 | 3.2 | 95.7 |
|  | 11.3 | 1.6 | 1.5 | 10 | 1.0 | 5.2 | 89.8 | 0.1 | 4.3 | 96.3 |
|  | 11.3 | 1.6 | 1.5 | 10 | 1.5 | 1.0 | 94.0 | 0.1 | 4.4 | 96.4 |
|  | 11.3 | 1.6 | 1.5 | 10 | 3.0 | 0.8 | 92.5 | 0.1 | 6.0 | 95.0 |
| 4* | 8.5 | 1.6 | 1.5 | 10 | 0.7 | 33.0 | 63.3 | 0.8 | 2.5 | 95.8 |
|  | 8.5 | 1.6 | 1.5 | 10 | 1.0 | 12.5 | 83.5 | 0.3 | 3.4 | 96.6 |
|  | 8.5 | 1.6 | 1.5 | 10 | 1.5 | 0.9 | 94.6 | 0.05 | 4.2 | 96.5 |
| 5* | 8.5 | 1.6 | 1.5 | 10 | 1.0 | 16.3 | 79.3 | 0.4 | 3.5 | 96.1 |
|  | 8.5 | 1.6 | 1.5 | 10 | 3.0 | 1.2 | 93.9 | 0.07 | 4.3 | 96.4 |
| 6* | 8.5 | 1.5 | 1.7 | 30 | 1.0 | 11.9 | 80.5 | 0.5 | 6.3 | 93.6 |
|  | 8.5 | 1.5 | 1.7 | 30 | 3.0 | 1.6 | 90.5 | 0.09 | 7.1 | 94.1 |
| 7* | 5.7 | 1.6 | 1.5 | 10 | 1.0 | 38.9 | 57.9 | 0.9 | 1.9 | 96.0 |
|  | 5.7 | 1.6 | 1.5 | 10 | 3.0 | 8.1 | 87.7 | 0.2 | 3.6 | 96.7 |
|  | 5.7 | 1.6 | 1.5 | 10 | 5.0 | 4.2 | 91.7 | 0.08 | 3.7 | 96.8 |
| 8* | 5.7 | 1.5 | 1.5 | 30 | 1.0 | 27.9 | 65.5 | 1.3 | 4.6 | 93.0 |
|  | 5.7 | 1.5 | 1.5 | 30 | 3.0 | 6.7 | 85.9 | 0.3 | 6.5 | 94.1 |
|  | 5.7 | 1.5 | 1.5 | 30 | 5.0 | 1.6 | 91.2 | 0.07 | 6.5 | 94.5 |
| 9 | 8.5 | 3.0 | 2.6 | 10 | 1.0 | 8.9 | 87.5 | 0.14 | 3.0 | 97.2 |
|  | 8.5 | 3.0 | 2.6 | 10 | 3.0 | 2.5 | 93.7 | 0.07 | 3.4 | 97.2 |
| 10 | 8.5 | 2.8 | 2.8 | 30 | 1.0 | 2.0 | 92.2 | 0.08 | 5.0 | 95.8 |
|  | 8.5 | 2.8 | 2.8 | 30 | 3.0 | 0.5 | 93.6 | 0.04 | 5.2 | 95.7 |
| 11 | 5.7 | 2.9 | 2.5 | 10 | 1.0 | 60.7 | 38.2 | 0.5 | 0.5 | 97.7 |
|  | 5.7 | 2.9 | 2.5 | 10 | 3.0 | 23.1 | 75.2 | 0.3 | 1.2 | 98.3 |
| 12 | 5.7 | 2.7 | 2.7 | 30 | 1.0 | 19.8 | 75.7 | 0.5 | 3.5 | 95.9 |
|  | 5.7 | 2.7 | 2.7 | 30 | 3.0 | 3.3 | 91.5 | 0.09 | 4.6 | 96.1 |
|  | 5.7 | 2.7 | 2.7 | 30 | 5.0 | 1.7 | 93.0 | 0.06 | 4.7 | 96.1 |

•2-TBP = 2-tert-butylphenol; 2,4-DTBP = 2,4-di-tert-butylphenol; 2,6-DTBP = 2,6-di-tert-butylphenol; 2,4,6-TTBP = 2,4,6-tri-butylphenol.
*not according to the invention

TABLE II

Production of 2,6-di-tert-butylphenol from 2-tert-butylphenol

| Example No. | Catalyst Amount (mmol) | Excess of isobutene (mol) | Solvent Type | Amount (ml) | Pressure (bar) | Reaction temp. (°C.) | Reaction time (hours) | 2-TBP | 2,6-DTBP | 2,4-DTBP | 2,4,6-TTBP• | Selectivity S |
|---|---|---|---|---|---|---|---|---|---|---|---|---|
| 13 | 8.5 | 2.7 | — |  | 2.8 | 30 | 1.0 | 2.6 | 91.5 | 0.1 | 5.1 | 95.6 |
|  | 8.5 | 2.7 |  |  | 2.8 | 30 | 3.0 | 0.6 | 93.6 | 0.04 | 5.3 | 95.7 |
| 14* | 8.5 | 3.2 | toluene | 100 | 2.6 | 30 | 1.0 | 5.5 | 88.8 | 0.2 | 4.9 | 95.5 |
|  | 8.5 | 3.2 | toluene | 100 | 2.6 | 30 | 3.0 | 1.1 | 92.9 | 0.1 | 5.3 | 95.6 |
|  | 8.5 | 3.2 | toluene | 100 | 2.6 | 30 | 5.0 | 0.7 | 93.2 | 0.07 | 5.4 | 95.5 |
| 15 | 8.5 | 3.4 | n-hexane | 100 | 2.6 | 30 | 1.0 | 8.6 | 87.8 | 0.2 | 2.9 | 97.2 |
|  | 8.5 | 3.4 | n-hexane | 100 | 2.6 | 30 | 3.0 | 1.4 | 94.8 | 0.05 | 3.3 | 97.3 |
|  | 8.5 | 3.4 | n-hexane | 100 | 2.6 | 30 | 5.0 | 0.9 | 95.2 | 0.05 | 3.4 | 97.2 |
| 16 | 8.5 | 3.3 | cyclohexane | 100 | 2.7 | 30 | 1.0 | 5.3 | 91.3 | 0.12 | 2.9 | 97.4 |
|  | 8.5 | 3.3 | cyclohexane | 100 | 2.7 | 30 | 3.0 | 1.0 | 95.3 | 0.06 | 3.1 | 97.4 |
|  | 8.5 | 3.3 | cyclohexane | 100 | 2.7 | 30 | 5.0 | 0.8 | 95.6 | 0.05 | 3.2 | 97.3 |
| 17 | 8.5 | 4.6 | cyclohexane | 200 | 2.6 | 30 | 1.0 | 11.7 | 86.0 | 0.2 | 1.9 | 98.0 |
|  | 8.5 | 4.6 | cyclohexane | 200 | 2.6 | 30 | 3.0 | 2.4 | 95.0 | 0.07 | 2.2 | 98.1 |
|  | 8.5 | 4.6 | cyclohexane | 200 | 2.6 | 30 | 5.0 | 1.0 | 96.4 | 0.04 | 2.2 | 98.1 |
| 18 | 5.7 | 2.8 | — |  | 2.8 | 30 | 1.0 | 18.9 | 76.6 | 0.5 | 3.5 | 95.8 |
|  | 5.7 | 2.8 |  |  | 2.8 | 30 | 3.0 | 3.2 | 91.7 | 0.09 | 4.5 | 96.2 |
|  | 5.7 | 2.8 |  |  | 2.8 | 30 | 5.0 | 1.6 | 93.9 | 0.07 | 4.5 | 96.2 |
| 19 | 5.7 | 3.3 | cyclohexane | 50 | 2.7 | 30 | 1.0 | 34.6 | 63.0 | 0.6 | 1.5 | 97.2 |
|  | 5.7 | 3.3 | cyclohexane | 50 | 2.7 | 30 | 3.0 | 10.4 | 86.4 | 0.2 | 2.6 | 97.5 |
|  | 5.7 | 3.3 | cyclohexane | 50 | 2.7 | 30 | 5.0 | 5.9 | 90.8 | 0.12 | 2.8 | 97.5 |
| 20 | 5.7 | 4.3 | cyclohexane | 100 | 2.7 | 30 | 1.0 | 50.9 | 47.6 | 0.6 | 0.7 | 97.6 |
|  | 5.7 | 4.3 | cyclohexane | 100 | 2.7 | 30 | 3.0 | 22.0 | 75.8 | 0.3 | 1.6 | 98.0 |
|  | 5.7 | 4.3 | cyclohexane | 100 | 2.7 | 30 | 5.0 | 14.7 | 83.0 | 0.2 | 1.8 | 98.1 |
| 21* | 8.5 | 1.6 | — |  | 1.5 | 10 | 1.0 | 23.1 | 72.8 | 0.6 | 3.0 | 96.1 |
|  | 8.5 | 1.6 |  |  | 1.5 | 10 | 3.0 | 1.7 | 93.7 | 0.1 | 4.1 | 96.6 |
|  | 8.5 | 1.6 |  |  | 1.5 | 10 | 5.0 | 0.9 | 94.1 | 0.1 | 4.4 | 96.4 |
| 22 | 8.5 | 1.8 | cyclohexane | 50 | 1.5 | 10 | 1.0 | 21.1 | 76.0 | 0.4 | 2.2 | 97.3 |
|  | 8.5 | 1.8 | cyclohexane | 50 | 1.5 | 10 | 3.0 | 1.8 | 94.7 | 0.1 | 3.0 | 97.5 |
| 23 | 8.5 | 1.8 | cyclohexane | 100 | 1.5 | 10 | 1.0 | 18.6 | 79.1 | 0.3 | 1.7 | 98.0 |
|  | 8.5 | 1.8 | cyclohexane | 100 | 1.5 | 10 | 3.0 | 1.6 | 95.7 | 0.09 | 2.3 | 98.1 |
|  | 8.5 | 1.8 | cyclohexane | 100 | 1.5 | 10 | 5.0 | 1.0 | 96.3 | 0.09 | 2.4 | 98.0 |
| 24 | 8.5 | 2.1 | cyclohexane | 200 | 1.5 | 10 | 1.0 | 25.5 | 73.0 | 0.3 | 1.0 | 98.5 |
|  | 8.5 | 2.1 | cyclohexane | 200 | 1.5 | 10 | 3.0 | 3.2 | 94.6 | 0.08 | 1.6 | 98.6 |
|  | 8.5 | 2.1 | cyclohexane | 200 | 1.5 | 10 | 5.0 | 1.3 | 96.7 | 0.06 | 1.6 | 98.7 |
| 25* | 8.5 | 1.1 | — |  | 1.7 | 30 | 1.0 | 14.7 | 78.2 | 0.6 | 5.8 | 93.8 |
|  | 8.5 | 1.1 |  |  | 1.7 | 30 | 3.0 | 2.7 | 89.4 | 0.12 | 7.1 | 94.0 |

TABLE II-continued

Production of 2,6-di-tert-butylphenol from 2-tert-butylphenol

| Example No. | Catalyst Amount (mmol) | Excess of isobutene (mol) | Solvent Type | Solvent Amount (ml) | Pressure (bar) | Reaction temp. (°C.) | Reaction time (hours) | 2-TBP | 2,6-DTBP | 2,4-DTBP | 2,4,6-TTBP• | Selectivity S |
|---|---|---|---|---|---|---|---|---|---|---|---|---|
|  | 8.5 | 1.1 | — |  | 1.7 | 30 | 5.0 | 1.2 | 90.9 | 0.08 | 7.1 | 94.1 |
| 26 | 8.5 | 1.1 | cyclohexane | 100 | 1.5 | 30 | 1.0 | 24.7 | 71.6 | 0.6 | 2.5 | 96.4 |
|  | 8.5 | 1.1 | cyclohexane | 100 | 1.5 | 30 | 3.0 | 6.1 | 87.8 | 0.2 | 3.5 | 96.7 |
|  | 8.5 | 1.1 | cyclohexane | 100 | 1.5 | 30 | 5.0 | 3.5 | 92.5 | 0.1 | 3.6 | 96.9 |
| 27 | 8.5 | 1.7 | cyclohexane | 200 | 1.5 | 30 | 1.0 | 44.9 | 53.3 | 0.6 | 0.9 | 97.6 |
|  | 8.5 | 1.7 | cyclohexane | 200 | 1.5 | 30 | 3.0 | 17.3 | 80.0 | 0.3 | 2.0 | 97.6 |
|  | 8.5 | 1.7 | cyclohexane | 200 | 1.5 | 30 | 5.0 | 10.3 | 86.9 | 0.2 | 2.2 | 97.8 |
| 28 | 5.7 | 3.9 | cyclohexane | 200 | 1.5 | 10 | 1.0 | 46.6 | 53.4 | 0.3 | 0.5 | 98.7 |
|  | 5.7 | 3.9 | cyclohexane | 200 | 1.5 | 10 | 3.0 | 9.5 | 89.0 | 0.1 | 1.2 | 98.8 |
|  | 5.7 | 3.9 | cyclohexane | 200 | 1.5 | 10 | 5.0 | 3.2 | 95.2 | 0.07 | 1.4 | 98.8 |
|  | 5.7 | 3.9 | cyclohexane | 200 | 1.5 | 10 | 22.0 | 0.7 | 97.6 | 0.07 | 1.5 | 98.7 |
| 29* | 8.5 | 1.1 | — |  | 1.5 | 30 | 1.0 | 23.6 | 69.8 | 1.1 | 4.9 | 93.4 |
|  | 8.5 | 1.1 |  |  | 1.5 | 30 | 3.0 | 5.1 | 87.3 | 0.3 | 6.5 | 94.2 |
|  | 8.5 | 1.1 |  |  | 1.5 | 30 | 5.0 | 1.7 | 90.3 | 0.14 | 7.1 | 94.0 |
| 30* | 8.5 | 1.3 | toluene | 100 | 1.5 | 30 | 1.0 | 24.5 | 68.8 | 1.2 | 4.6 | 93.5 |
|  | 8.5 | 1.3 | toluene | 100 | 1.5 | 30 | 3.0 | 4.1 | 88.2 | 0.3 | 6.8 | 94.0 |
|  | 8.5 | 1.3 | toluene | 100 | 1.5 | 30 | 5.0 | 1.7 | 90.5 | 0.2 | 6.9 | 94.1 |

•2-TBP = 2-tert-butylphenol; 2,4-DTBP = 2,4-di-tert-butylphenol; 2,6-DTBP = 2,6-di-tert-butylphenol; 2,4,6-TTBP = 2,4,6-tri-butylphenol.
*not according to the invention

TABLE III

Production of 2,6-di-tert-butylphenol from 2-tert-butylphenol

| Example No. | Catalyst Amount (mmol) | Excess of isobutene (mol) | Solvent Type | Solvent Amount (ml) | Pressure (bar) | Reaction temp. (°C.) | Reaction time (hours) | 2-TBP | 2,6-DTBP | 2,4-DTBP | 2,4,6-TTBP• | Selectivity S |
|---|---|---|---|---|---|---|---|---|---|---|---|---|
| 31* | 8.5 | 1.0 | — |  | 1.5 | 30 | 1.0 | 29.2 | 64.6 | 1.2 | 4.4 | 93.3 |
|  | 8.5 | 1.0 |  |  | 1.5 | 30 | 3.0 | 5.9 | 86.6 | 0.3 | 6.5 | 94.1 |
|  | 8.5 | 1.0 |  |  | 1.5 | 30 | 5.0 | 2.4 | 90.0 | 0.15 | 6.7 | 94.3 |
| 32* | 8.5 | 1.3 | m-xylene | 100 | 1.5 | 30 | 1.0 | 29.3 | 65.4 | 1.2 | 3.6 | 94.2 |
|  | 8.5 | 1.3 | m-xylene | 100 | 1.5 | 30 | 3.0 | 5.1 | 87.9 | 0.3 | 6.1 | 94.5 |
|  | 8.5 | 1.3 | m-xylene | 100 | 1.5 | 30 | 5.0 | 2.0 | 90.8 | 0.14 | 6.5 | 94.5 |
| 33* | 8.5 | 1.8 | m-xylene | 100 | 1.5 | 10 | 1.0 | 30.3 | 66.3 | 0.7 | 2.3 | 96.4 |
|  | 8.5 | 1.8 | m-xylene | 100 | 1.5 | 10 | 3.0 | 2.3 | 93.4 | 0.1 | 3.8 | 96.8 |
|  | 8.5 | 1.8 | m-xylene | 100 | 1.5 | 10 | 5.0 | 0.9 | 94.6 | 0.08 | 4.0 | 96.7 |
| 34 | 8.5 | 1.8 | hexane | 100 | 1.5 | 10 | 1.0 | 20.7 | 76.5 | 0.4 | 2.0 | 97.5 |
|  | 8.5 | 1.8 | hexane | 100 | 1.5 | 10 | 3.0 | 1.6 | 95.3 | 0.07 | 2.8 | 97.7 |
|  | 8.5 | 1.8 | hexane | 100 | 1.5 | 10 | 5.0 | 0.8 | 96.0 | 0.07 | 2.8 | 97.7 |
| 35 | 8.5 | 1.9 | hexane | 200 | 1.5 | 10 | 1.0 | 29.8 | 68.3 | 0.4 | 1.3 | 98.0 |
|  | 8.5 | 1.9 | hexane | 200 | 1.5 | 10 | 3.0 | 4.5 | 93.0 | 0.08 | 2.1 | 98.2 |
|  | 8.5 | 1.9 | hexane | 200 | 1.5 | 10 | 5.0 | 1.7 | 95.7 | 0.06 | 2.2 | 98.2 |
| 36* | 8.5 | 1.3 | — | — | 1.5 | 30 | 1.0 | 5.6 | 85.7 | 0.3 | 7.6 | 93.2 |
|  | 8.5 | 1.3 |  |  | 1.5 | 30 | 3.0 | 1.7 | 88.5 | 0.4 | 8.5 | 92.6 |
|  | 8.5 | 1.3 |  |  | 1.5 | 30 | 5.0 | 1.3 | 88.9 | 0.4 | 8.6 | 92.6 |
| 37 | 8.5 | 2.3 | cyclohexane | 200 | 1.5 | 10 | 1.0 | 5.7 | 92.4 | 0.1 | 1.6 | 98.5 |
|  | 8.5 | 2.3 | cyclohexane | 200 | 1.5 | 10 | 3.0 | 2.0 | 95.6 | 0.14 | 2.0 | 98.2 |
|  | 8.5 | 2.3 | cyclohexane | 200 | 1.5 | 10 | 5.0 | 2.0 | 95.5 | 0.15 | 2.1 | 98.2 |
| 38 | 5.7 | 2.4 | cyclohexane | 200 | 1.5 | 10 | 1.0 | 15.9 | 82.5 | 0.16 | 1.2 | 98.7 |
|  | 5.7 | 2.4 | cyclohexane | 200 | 1.5 | 10 | 3.0 | 1.5 | 96.3 | 0.1 | 1.8 | 98.5 |
|  | 5.7 | 2.4 | cyclohexane | 200 | 1.5 | 10 | 5.0 | 1.5 | 96.3 | 0.1 | 1.8 | 98.5 |
| 39 | 3.8 | 1.8 | cyclohexane | 200 | 1.5 | 10 | 1.0 | 39.8 | 58.9 | 0.3 | 0.7 | 98.6 |
|  | 3.8 | 1.8 | cyclohexane | 200 | 1.5 | 10 | 3.0 | 8.0 | 90.1 | 0.13 | 1.5 | 98.6 |
|  | 3.8 | 1.8 | cyclohexane | 200 | 1.5 | 10 | 5.0 | 3.0 | 94.9 | 0.06 | 1.7 | 98.6 |
|  | 3.8 | 1.8 | cyclohexane | 200 | 1.5 | 10 | 11.0 | 0.8 | 97.0 | 0.05 | 1.9 | 98.4 |
| 40 | 2.8 | 1.8 | cyclohexane | 200 | 1.5 | 10 | 1.0 | 63.6 | 35.6 | 0.3 | 0.3 | 98.5 |
|  | 2.8 | 1.8 | cyclohexane | 200 | 1.5 | 10 | 5.0 | 10.5 | 87.8 | 0.1 | 1.3 | 98.7 |
|  | 2.8 | 1.8 | cyclohexane | 200 | 1.5 | 10 | 12.0 | 2.5 | 95.6 | 0.04 | 1.6 | 98.7 |
|  | 2.8 | 1.8 | cyclohexane | 200 | 1.5 | 10 | 22.0 | 0.8 | 97.3 | 0.03 | 1.6 | 98.7 |
| 41 | 1.9 | 1.7 | cyclohexane | 200 | 1.5 | 10 | 1.0 | 81.1 | 18.5 | 0.2 | 0.1 | 98.5 |
|  | 1.9 | 1.7 | cyclohexane | 200 | 1.5 | 10 | 5.0 | 30.8 | 67.9 | 0.3 | 0.9 | 98.5 |
|  | 1.9 | 1.7 | cyclohexane | 200 | 1.5 | 10 | 12.0 | 8.4 | 89.9 | 0.09 | 1.4 | 98.7 |
|  | 1.9 | 1.7 | cyclohexane | 200 | 1.5 | 10 | 21.0 | 3.6 | 94.6 | 0.05 | 1.5 | 98.7 |
|  | 1.9 | 1.7 | cyclohexane | 200 | 1.5 | 10 | 49.0 | 1.0 | 97.1 | 0.02 | 1.6 | 98.7 |
| 42* | 5.7 | 2.0 | xylene | 200 | 1.5 | 10 | 1.0 | 15.1 | 81.0 | 0.4 | 3.1 | 96.6 |
|  | 5.7 | 2.0 | xylene | 200 | 1.5 | 10 | 3.0 | 1.1 | 94.3 | 0.1 | 4.1 | 96.6 |
|  | 5.7 | 2.0 | xylene | 200 | 1.5 | 10 | 5.0 | 0.9 | 93.9 | 0.1 | 4.7 | 96.1 |
| 43* | 5.7 | 1.0 | — |  | 1.5 | 50 | 1.0 | 20.4 | 68.4 | 1.5 | 8.6 | 89.2 |
|  | 5.7 | 1.0 |  |  | 1.5 | 50 | 3.0 | 3.7 | 83.7 | 0.5 | 11.0 | 90.1 |
|  | 5.7 | 1.0 |  |  | 1.5 | 50 | 5.0 | 2.3 | 85.1 | 0.3 | 11.2 | 90.3 |
| 44 | 5.7 | 1.2 | hexane | 400 | 1.5 | 50 | 1.0 | 36.3 | 61.0 | 0.7 | 1.6 | 96.9 |
|  | 5.7 | 1.2 | hexane | 400 | 1.5 | 50 | 3.0 | 12.0 | 84.4 | 0.3 | 2.9 | 97.0 |
|  | 5.7 | 1.2 | hexane | 400 | 1.5 | 50 | 5.0 | 7.2 | 88.9 | 0.2 | 3.2 | 97.0 |
|  | 5.7 | 1.2 | hexane | 400 | 1.5 | 50 | 22.0 | 2.2 | 93.0 | 0.1 | 3.6 | 97.0 |

TABLE III-continued

Production of 2,6-di-tert-butylphenol from 2-tert-butylphenol

| Example No. | Catalyst Amount (mmol) | Excess of isobutene (mol) | Solvent Type | Amount (ml) | Pressure (bar) | Reaction temp. (°C.) | Reaction time (hours) | 2-TBP | 2,6-DTBP | 2,4-DTBP | 2,4,6-TTBP• | Selectivity S |
|---|---|---|---|---|---|---|---|---|---|---|---|---|
| 45 | 5.7 | 2.1 | hexane | 400 | 1.5 | 10 | 1.0 | 32.1 | 66.4 | 0.3 | 0.8 | 98.6 |
|  | 5.7 | 2.1 | hexane | 400 | 1.5 | 10 | 3.0 | 9.4 | 88.9 | 0.1 | 1.3 | 98.7 |
|  | 5.7 | 2.1 | hexane | 400 | 1.5 | 10 | 5.0 | 4.0 | 94.2 | 0.07 | 1.5 | 98.7 |
|  | 5.7 | 2.1 | hexane | 400 | 1.5 | 10 | 22.0 | 1.2 | 96.3 | 0.20 | 2.0 | 98.2 |
| 46 | 8.5 | 4.8 | hexane | 800 | 1.5 | 10 | 1.0 | 25.0 | 73.9 | 0.2 | 0.7 | 99.0 |
|  | 8.5 | 4.8 | hexane | 800 | 1.5 | 10 | 3.0 | 6.3 | 92.3 | 0.09 | 1.1 | 99.0 |
|  | 8.5 | 4.8 | hexane | 800 | 1.5 | 10 | 5.0 | 3.0 | 95.3 | 0.09 | 1.3 | 98.8 |
|  | 8.5 | 4.8 | hexane | 800 | 1.5 | 10 | 22.0 | 1.9 | 96.0 | 0.1 | 1.5 | 98.6 |

•2-TBP = 2-tert-butylphenol; 2,4-DTBP = 2,4-di-tert-butylphenol, 2,6-DTBP = 2,6-di-tert-butylphenol; 2,4,6-TTBP = 2,4,6-tri-butylphenol.
*not according to the invention

TABLE IV

Production of 2,6-di-tert-butylphenol from 2-tert-butylphenol

| Example No. | Catalyst Amount (mmol) | Excess of isobutene (mol) | Solvent Type | Amount (ml) | Pressure (bar) | Reaction temp. (°C.) | Reaction time (hours) | 2-TBP | 2,6-DTBP | 2,4-DTBP | 2,4,6-TTBP• | Selectivity S |
|---|---|---|---|---|---|---|---|---|---|---|---|---|
| 47* | 5.7 | 1.3 | — |  | 1.4 | 10 | 1.0 | 21.1 | 73.8 | 0.7 | 3.8 | 95.2 |
|  | 5.7 | 1.3 |  |  | 1.4 | 10 | 3.0 | 1.1 | 92.9 | 0.2 | 5.3 | 95.5 |
|  | 5.7 | 1.3 |  |  | 1.4 | 10 | 5.0 | 0.8 | 93.4 | 0.13 | 5.1 | 95.8 |
| 48 | 5.7 | 1.6 | hexane | 1250 | 1.5 | 10 | 1.0 | 68.7 | 39.4 | 0.2 | 0.2 | 99.1 |
|  | 5.7 | 1.6 | hexane | 1250 | 1.5 | 10 | 3.0 | 29.0 | 70.0 | 0.2 | 0.6 | 99.0 |
|  | 5.7 | 1.6 | hexane | 1250 | 1.5 | 10 | 5.0 | 15.3 | 83.5 | 0.14 | 0.9 | 99.0 |
|  | 5.7 | 1.6 | hexane | 1250 | 1.5 | 10 | 22.0 | 2.0 | 96.3 | 0.07 | 1.3 | 98.9 |
| 49 | 8.5 | 1.8 | hexane | 1250 | 1.5 | 10 | 1.0 | 49.4 | 49.9 | 0.2 | 0.3 | 99.1 |
|  | 8.5 | 1.8 | hexane | 1250 | 1.5 | 10 | 3.0 | 18.0 | 80.8 | 0.15 | 0.8 | 99.0 |
|  | 8.5 | 1.8 | hexane | 1250 | 1.5 | 10 | 5.0 | 9.0 | 89.7 | 0.1 | 1.1 | 98.9 |
|  | 8.5 | 1.8 | hexane | 1250 | 1.5 | 10 | 22.0 | 2.0 | 96.3 | 0.09 | 1.4 | 98.8 |
| 50 | 8.9 | 1.6 | hexane | 830 | 1.5 | 50 | 1.0 | 32.7 | 65.5 | 0.4 | 1.0 | 98.2 |
|  | 8.9 | 1.6 | hexane | 830 | 1.5 | 50 | 3.0 | 9.1 | 88.2 | 0.3 | 2.1 | 97.8 |
|  | 8.9 | 1.6 | hexane | 830 | 1.5 | 50 | 5.0 | 4.3 | 93.0 | 0.2 | 2.2 | 98.0 |
|  | 8.9 | 1.6 | hexane | 830 | 1.5 | 50 | 22.0 | 2.4 | 94.2 | 0.3 | 2.7 | 97.5 |
| 51 | 8.9 | 2.3 | hexane | 830 | 1.5 | 30 | 1.0 | 23.4 | 75.3 | 0.2 | 0.9 | 98.8 |
|  | 8.9 | 2.3 | hexane | 830 | 1.5 | 30 | 3.0 | 5.0 | 93.1 | 0.1 | 1.5 | 98.6 |
|  | 8.9 | 2.3 | hexane | 830 | 1.5 | 30 | 5.0 | 2.5 | 95.5 | 0.1 | 1.6 | 98.6 |
|  | 8.9 | 2.3 | hexane | 830 | 1.5 | 30 | 7.0 | 1.8 | 96.1 | 0.1 | 1.7 | 98.5 |
| 52 | 8.9 | 2.6 | hexane | 830 | 1.5 | 10 | 1.0 | 37.6 | 61.5 | 0.25 | 0.5 | 99.0 |
|  | 8.9 | 2.6 | hexane | 830 | 1.5 | 10 | 3.0 | 12.8 | 85.9 | 0.14 | 0.9 | 99.0 |
|  | 8.9 | 2.6 | hexane | 830 | 1.5 | 10 | 5.0 | 6.5 | 92.2 | 0.1 | 1.1 | 99.0 |
|  | 8.9 | 2.6 | hexane | 830 | 1.5 | 10 | 21.0 | 2.0 | 96.3 | 0.14 | 1.3 | 98.8 |
| 53 | 8.5 | 2.0 | — |  | 1.5 | 10 | 1.0 | 2.0 | 92.1 | 0.05 | 5.2 | 95.7 |
|  | 8.5 | 2.0 |  |  | 1.5 | 10 | 3.0 | 1.3 | 91.8 | 0.07 | 6.2 | 94.9 |
|  | 8.5 | 2.0 |  |  | 1.5 | 10 | 5.0 | 1.3 | 91.0 | 0.09 | 6.9 | 94.3 |
| 54* | 5.7 | 1.7 | — |  | 1.5 | 10 | 1.0 | 17.7 | 78.0 | 0.15 | 3.7 | 96.2 |
|  | 5.7 | 1.7 |  |  | 1.5 | 10 | 3.0 | 1.2 | 93.3 | 0.03 | 4.6 | 96.2 |
|  | 5.7 | 1.7 |  |  | 1.5 | 10 | 5.0 | 0.8 | 93.8 | 0.03 | 4.8 | 96.1 |
|  | 5.7 | 1.7 |  |  | 1.5 | 10 | 21.0 | 0.7 | 92.8 | 0.07 | 5.3 | 95.6 |
| 55 | 5.7 | 2.2 | ethyl-cyclohexane | 200 | 1.5 | 10 | 2.0 | 35.4 | 63.2 | 0.3 | 0.9 | 98.4 |
|  | 5.7 | 2.2 | ethyl-cyclohexane | 200 | 1.5 | 10 | 3.0 | 7.6 | 90.3 | 0.04 | 1.8 | 98.4 |
|  | 5.7 | 2.2 | ethyl-cyclohexane | 200 | 1.5 | 10 | 5.0 | 3.2 | 94.5 | 0.05 | 1.9 | 98.4 |
|  | 5.7 | 2.2 | ethyl-cyclohexane | 200 | 1.5 | 10 | 7.0 | 1.7 | 95.9 | 0.03 | 2.0 | 98.4 |
|  | 5.7 | 2.2 | ethyl-cyclohexane | 200 | 1.5 | 10 | 69.0 | 1.0 | 95.7 | 0.08 | 2.9 | 97.6 |
| 56 | 5.7 | 1.8 | isopropylcyclohexane | 200 | 1.5 | 10 | 1.0 | 32.8 | 65.5 | 0.3 | 1.1 | 98.3 |
|  | 5.7 | 1.8 | isopropylcyclohexane | 200 | 1.5 | 10 | 3.0 | 6.8 | 90.9 | 0.04 | 1.8 | 98.4 |
|  | 5.7 | 1.8 | isopropylcyclohexane | 200 | 1.5 | 10 | 5.0 | 2.7 | 95.0 | 0.03 | 2.0 | 98.3 |
|  | 5.7 | 1.8 | isopropylcyclohexane | 200 | 1.5 | 10 | 21.0 | 0.9 | 96.2 | 0.07 | 2.5 | 97.9 |
| 57 | 5.7 | 1.8 | dekalin | 200 | 1.5 | 10 | 1.0 | 32.5 | 65.8 | 0.3 | 1.1 | 98.3 |
|  | 5.7 | 1.8 | dekalin | 200 | 1.5 | 10 | 3.0 | 6.7 | 91.1 | 0.04 | 1.8 | 98.4 |
|  | 5.7 | 1.8 | dekalin | 200 | 1.5 | 10 | 5.0 | 2.6 | 95.1 | 0.03 | 2.0 | 98.3 |
|  | 5.7 | 1.8 | dekalin | 200 | 1.5 | 10 | 21.0 | 0.9 | 96.1 | 0.07 | 2.4 | 98.0 |
| 58* | 5.7 | 1.9 | toluene | 200 | 1.5 | 10 | 1.0 | 29.9 | 66.5 | 0.7 | 2.5 | 96.1 |
|  | 5.7 | 1.9 | toluene | 200 | 1.5 | 10 | 3.0 | 2.8 | 92.0 | 0.05 | 4.1 | 96.6 |
|  | 5.7 | 1.9 | toluene | 200 | 1.5 | 10 | 5.0 | 0.9 | 93.8 | 0.04 | 4.8 | 96.1 |
|  | 5.7 | 1.9 | toluene | 200 | 1.5 | 10 | 21.0 | 0.8 | 93.8 | 0.05 | 4.8 | 96.1 |

TABLE IV-continued

Production of 2,6-di-tert-butylphenol from 2-tert-butylphenol

| Example No. | Catalyst Amount (mmol) | Excess of isobutene (mol) | Solvent Type | Amount (ml) | Pressure (bar) | Reaction temp. (°C.) | Reaction time (hours) | Composition of the reaction (% by weight) | | | | Selectivity S |
|---|---|---|---|---|---|---|---|---|---|---|---|---|
| | | | | | | | | 2-TBP | 2,6-DTBP | 2,4-DTBP | 2,4,6-TTBP• | |
| 59* | 5.7 | 2.6 | m-xylene | 200 | 1.5 | 10 | 1.0 | 20.7 | 76.0 | 0.2 | 2.6 | 97.1 |
| | 5.7 | 2.6 | m-xylene | 200 | 1.5 | 10 | 3.0 | 0.9 | 94.6 | 0.04 | 4.0 | 96.7 |
| | 5.7 | 2.6 | m-xylene | 200 | 1.5 | 10 | 5.0 | 0.8 | 94.5 | 0.05 | 4.2 | 96.6 |

•2-TBP = 2-tert-butylphenol; 2,4-DTBP = 2,4-di-tert-butylphenol; 2,6-DTBP = 2,6-di-tert-butylphenol; 2,4,6-TTBP = 2,4,6-tri-butylphenol.
*not according to the invention

TABLE V

Production of 2,6-di-tert-butylphenol from 2-tert-butylphenol

| Example No. | Catalyst Amount (mmol) | Excess of isobutene (mol) | Solvent Type | Amount (ml) | Pressure (bar) | Reaction temp. (°C.) | Reaction time (hours) | Composition of the reaction (% by weight) | | | | High Boilers (% by wt.) |
|---|---|---|---|---|---|---|---|---|---|---|---|---|
| | | | | | | | | 2-TBP | 2,6-DTBP | 2,4-DTBP | 2,4,6-TTBP• | |
| 60* | 5.7 | 1.7 | — | | 1.5 | 10 | 1.0 | 20.7 | 74.9 | 0.2 | 3.7 | |
| | 5.7 | 1.7 | | | 1.5 | 10 | 3.0 | 1.5 | 93.1 | 0.07 | 4.8 | |
| | 5.7 | 1.7 | | | 1.5 | 10 | 5.0 | 0.8 | 93.4 | 0.05 | 5.1 | |
| | 5.7 | 1.7 | | | 1.5 | 10 | 50.0 | 0.8 | 91.2 | 0.09 | 7.3 | |
| | 5.7 | 1.7 | | | 1.5 | 10 | 70.0 | 0.7 | 90.6 | 0.07 | 7.9 | |
| 61 | 5.7 | 2.0 | cyclohexane | 200 | 1.5 | 10 | 1.0 | 48.3 | 50.1 | 0.4 | 0.7 | — |
| | 5.7 | 2.0 | cyclohexane | 200 | 1.5 | 10 | 3.0 | 15.6 | 82.1 | 0.09 | 1.7 | — |
| | 5.7 | 2.0 | cyclohexane | 200 | 1.5 | 10 | 5.0 | 6.7 | 90.5 | 0.05 | 2.2 | — |
| | 5.7 | 2.0 | cyclohexane | 200 | 1.5 | 10 | 22.0 | 1.0 | 95.8 | 0.03 | 2.5 | — |
| 62 | 5.7 | 2.0 | cyclooctene | 200 | 1.5 | 10 | 1.0 | 32.2 | 63.1 | 0.4 | 1.1 | 2.7 |
| | 5.7 | 2.0 | cyclooctene | 200 | 1.5 | 10 | 3.0 | 6.9 | 87.9 | 0.13 | 2.0 | 2.7 |
| | 5.7 | 2.0 | cyclooctene | 200 | 1.5 | 10 | 5.0 | 2.5 | 92.4 | 0.03 | 2.2 | 2.6 |
| | 5.7 | 2.0 | cyclooctene | 200 | 1.5 | 10 | 22.0 | 1.1 | 93.5 | 0.07 | 2.5 | 2.5 |
| 63 | 5.7 | 1.9 | octene-1 | 200 | 1.5 | 10 | 1.0 | 32.8 | 62.8 | 0.4 | 1.2 | 2.3 |
| | 5.7 | 1.9 | octene-1 | 200 | 1.5 | 10 | 3.0 | 6.8 | 88.3 | 0.05 | 2.2 | 2.3 |
| | 5.7 | 1.9 | octene-1 | 200 | 1.5 | 10 | 5.0 | 2.6 | 92.4 | 0.03 | 2.4 | 2.2 |
| | 5.7 | 1.9 | octene-1 | 200 | 1.5 | 10 | 22.0 | 0.9 | 93.7 | 0.06 | 2.7 | 2.1 |

•2-TBP = 2-tert-butylphenol; 2,4-DTBP = 2,4-di-tert-butylphenol; 2,6-DTBP = 2,6-di-tert-butylphenol; 2,4,6-TTBP = 2,4,6-tri-butylphenol.
*not according to the invention The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of 2,6-di-tert-butylphenol by reaction of 2-tert-butylphenol with isobutene in the liquid phase in the presence of aluminum tris-(2-tert-butylphenolate) as a catalyst, wherein the reaction is conducted in a diluent being:
   (a) a member selected from the group consisting of saturated aliphatic hydrocarbons; saturate cycloaliphatic hydrocarbons; $C_5$-$C_{16}$ alkenes of the formulae $R_1$—CH=$CH_2$ or $R_2$—CH=CH—$R_3$, in which $R_1$, $R_2$, and $R_3$ represent alkyl or $R_2$ and $R_3$ form a $C_5$—$C_{12}$-cycloalkene; and mixtures thereof; said member being present in a quantity of 20–1000 parts by weight, based on 100 parts by weight of 2-tert-butylphenol;
   (b) a mixture of (i) a member selected from the group consisting of saturated aliphatic hydrocarbons; saturated cycloaliphatic hydrocarbons; $C_5$-$C_{16}$-alkenes of the formulae $R_1$—CH=$CH_2$ or $R_2$—CH=CH—$R_3$, in which $R_1$, $R_2$ and $R_3$ represent alkyl or $R_2$ and $R_3$ form a $C_5$—$C_{12}$-cycloalkene; and mixtures thereof; said member being present in a quantity of 20–1000 parts by weight, based on 100 parts by weight of 2-tert-butylphenol, and (ii) dissolved isobutene in a molar excess of 0.2–10 mols based on 1 mole of 2-tert-butylphenol; or
   (c) an excess of liquid isobutene, said molar excess being from 2–10 moles, based on 1 mole of tert-butylphenol, said reaction being conducted at 0°–80° C., a pressure of 0.1–11 bars, and with a catalyst concentration of 0.005–5 mol%, based on the 2-tert-butylphenol.

2. A process according to claim 1, wherein the diluent comprises at least one saturated aliphatic hydrocarbon, or at least one saturated cycloaliphatic hydrocarbon, or at least one $C_5$ to $C_{16}$ alkene, or at least one $C_5$ to $C_{12}$ cycloalkene, or mixtures thereof, in an amount of 20 to 1,000 parts by weight per 100 parts by weight of 2-tert-butylphenol, and a molar excess of isobutene in an amount of 0.2 to 10 moles per mole of 2-tert-butylphenol.

3. A process according to claim 1, wherein the reaction is performed in the presence of an excess of isobutene of 2 to 10 moles per mole of 2-tert-butylphenol, said excess isobutene being the diluent.

4. A process according to claim 1, wherein the diluent comprises hexane, cyclohexane, ethylcyclohexane, isopropylcyclohexane, decalin or mixtures thereof.

5. A process according to claim 1, wherein the diluent comprises 40 to 500 parts by weight of diluent constituent other than isobutene, per 100 parts by weight of 2-tert-butylphenol, and isobutene in a molar excess of 1 to 5 mole per mole of 2-tert-butylphenol.

6. A process according to claim 1, wherein the diluent comprises 60 to 200 parts by weight of diluent constituent other than isobutene, per 100 parts by weight of 2-tert-butylphenol, and isobutene in an excess of 1.1 to 2.5 moles per mole of 2-tert-butylphenol.

7. A process according to claim 1, wherein the reaction is performed in the presence of a molar excess of isobutene of 2.2 to 5 moles per mole of 2-tert-butylphenol.

8. A process according to claim 1, wherein the reaction is performed at temperatures of 5° C. to 50° C. and at pressures of 0.2 bar to 6 bars.

9. A process according to claim 1, wherein the reaction is performed at temperatures of 10° C. to 20° C.

10. A process according to claims 1 and 8, wherein the reaction is performed at pressures of 0.5 bar to 2.5 bars.

11. A process according to claim 1, wherein aluminum tris-(2-tert-butylphenolate) is used as a catalyst in amounts of 0.05 to 0.8 mol%, based on the 2-tert-butylphenol.

12. A process according to claim 1, wherein aluminum tris-(2-tert-butylphenolate) is used as a catalyst in amounts of 0.1 to 0.5 mol%, based on the 2-tert-butylphenol used.

13. A process of claim 1, wherein the saturated aliphatic hydrocarbons and saturated cycloaliphatic hydrocarbons have from 5 to 10 carbon atoms.

14. A process for the production of 2,6-di-tert-butylphenol by reaction of 2-tert-butylphenol with isobutene in the liquid phase at temperatures in the range of 5° C. to 50° C. and pressures of from 0.2 bar to 6 bars in the presence of 0.05 to 0.8 mol% of aluminum tris-(2-tert-butylphenolate), based on the 2-tert-butylphenol, wherein the reaction is conducted in a diluent being:

(a) a member selected from the group consisting of saturated aliphatic hydrocarbons; saturated cycloaliphatic hydrocarbons; $C_5-C_{16}$ alkenes of the formulae $R_1-CH=CH_2$ or $R_2-CH=CH-R_3$, in which $R_1$, $R_2$, and $R_3$ represent alkyl or $R_2$ and $R_3$ form a $C_5-C_{12}$-cycloalkene; and mixtures thereof; said member being present in a quantity of 20–1000 parts by weight, based on 100 parts by weight of 2-tert-butylphenol;

(b) a mixture of (i) a member selected from the group consisting of saturated aliphatic hydrocarbons; saturated cycloaliphatic hydrocarbons; $C_5-C_{16}$ alkenes of the formulae $R_1-CH=CH_2$ or $R_2-CH=CH-R_3$, in which $R_1$, $R_2$ and $R_3$ represent alkyl or $R_2$ and $R_3$ form a $C_5-C_{12}$ cycloalkene; and mixtures thereof; said member being present in a quantity of 20–1000 parts by weight, based on 100 parts by weight of 2-tert-butylphenol, and (ii) dissolved isobutene in a molar excess of 0.2–10 mols based on 1 mol of 2-tert-butylphenol; or (c) an excess of liquid isobutene, said molar excess being from 2–10 moles, based on 1 mole of tert-butylphenol.

15. A process of claim 14, wherein the reaction temperature is 5° C. to 50° C., the pressure is 0.5 to 2.5 bars and from 60 to 200 parts by weight diluent per 100 parts by weight of 2-tert-butylphenol are used.

16. A process of claim 14, wherein the diluent is cyclohexane, ethylcyclohexane, isopropylcyclohexane or decalin.

17. A process of claim 14, wherein the pressure is 0.5 to 2.8 bars and isobutene is used in molar excess as a diluent in an amount of from 2.2 to 5 moles per mole of 2-tert-butylphenol.

18. A process of claim 1, wherein the aluminum tris-(2-tertbutyl phenolate) is formed in the reaction mixture from aluminum compounds.

19. A process according to claim 8, wherein the reaction is performed at pressures of 0.5 bar to 2.5 bars.

* * * * *